US00PP23963P2

(12) United States Plant Patent
Strooper

(10) Patent No.: US PP23,963 P2
(45) Date of Patent: Oct. 8, 2013

(54) TRADESCANTIA PLANT NAMED 'GOOD LUCK'

(50) Latin Name: *Tradescantia andersoniana*
Varietal Denomination: Good Luck

(75) Inventor: Jan Strooper, Anna Paulowna (NL)

(73) Assignee: Compass Plants B.V., Hillegom (NL)

( * ) Notice: Subject to any disclaimer, the term of this patent is extended or adjusted under 35 U.S.C. 154(b) by 357 days.

(21) Appl. No.: 13/065,260

(22) Filed: Mar. 17, 2011

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP14,824 P2 * 5/2004 Richards ..... Plt./263.1

OTHER PUBLICATIONS

Pluto UPOV Citations for 'Good Luck' Accessed May 6, 2013.*

* cited by examiner

*Primary Examiner* — Wendy C Haas
(74) *Attorney, Agent, or Firm* — C. A. Whealy

(57) ABSTRACT

A new and distinct cultivar of *Tradescantia* plant named 'Good Luck', characterized by its compact and upright plant habit; strong and healthy leaves; freely flowering habit; purple-colored flowers; long flowering period; and good garden performance.

2 Drawing Sheets

Botanical designation: *Tradescantia andersoniana.*
Cultivar denomination: 'GOOD LUCK'.

BACKGROUND OF THE INVENTION

The present invention relates to a new and distinct cultivar of *Tradescantia* plant, botanically known as *Tradescantia andersoniana* and hereinafter referred to by the name 'Good Luck'.

The new *Tradescantia* plant is a product of a planned breeding program conducted by the Inventor in Anna Paulowna, The Netherlands. The objective of the breeding program was to create new compact *Tradescantia* plants with attractive flower coloration.

The new *Tradescantia* plant originated from a cross-pollination made by the Inventor in 2004 in Anna Paulowna, The Netherlands, of two unnamed seedling selections of *Tradescantia andersoniana*, not patented. The new *Tradescantia* plant was discovered and selected by the Inventor as a single flowering plant from within the progeny of the stated cross-pollination in a controlled environment in Anna Paulowna, The Netherlands in 2006.

Asexual reproduction of the new *Tradescantia* plant by cuttings in a controlled environment in Anna Paulowna, The Netherlands since 2006 has shown that the unique features of this new *Tradescantia* plant are stable and reproduced true to type in successive generations.

SUMMARY OF THE INVENTION

Plants of the new *Tradescantia* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Good Luck'. These characteristics in combination distinguish 'Good Luck' as a new and distinct *Tradescantia* plant:

1. Compact and upright plant habit.
2. Strong and healthy leaves.
3. Freely flowering habit.
4. Purple-colored flowers.
5. Long flowering period.
6. Good garden performance.

Plants of the new *Tradescantia* and the parent selections differ primarily in plant size as plants of the new *Tradescantia* are more compact than plants of the parent selections.

Plants of the new *Tradescantia* can be compared to plants of the *Tradescantia andersoniana* 'Bilberry Ice', not patented. In side-by-side comparisons conducted in Anna Paulowna, The Netherlands, plants of the new *Tradescantia* and 'Bilberry Ice' differed in the following characteristics:

1. Plants of the new *Tradescantia* were more compact than plants of 'Bilberry Ice'.
2. Leaves of plants of the new *Tradescantia* were stronger and healthier than leaves of plants of 'Bilberry Ice'.
3. Plants of the new *Tradescantia* were more freely flowering than plants of 'Bilberry Ice'.
4. Plants of the new *Tradescantia* flowered for a longer period of time than plants of 'Bilberry Ice'.

BRIEF DESCRIPTION OF THE PHOTOGRAPHS

The accompanying colored photographs illustrate the overall appearance of the new *Tradescantia* plant showing the colors as true as it is reasonably possible to obtain in colored reproductions of this type. Colors in the photographs may differ slightly from the color values cited in the detailed botanical description which accurately describe the colors of the new *Tradescantia* plant.

The photograph on the first sheet comprises a side perspective view of a typical flowering plant of 'Good Luck' grown in a container.

The photograph at the top of the second sheet is a close-up view of a typical flower of 'Good Luck'.

The photograph at the bottom of the second sheet is a close-up view of the upper surface of typical leaves of 'Good Luck'.

DETAILED BOTANICAL DESCRIPTION

The aforementioned photographs and following observations, measurements and values describe plants grown in two-liter containers during the late summer in an outdoor nursery in Boskoop, The Netherlands and under commercial cultural practices. During the production of the plants, day temperatures ranged from 10° C. to 25° C. and night temperatures ranged from 4° C. to 16° C. Plants were two years old when the photographs and description were taken. In the following description, color references are made to The Royal Horticultural Society Colour Chart, 2007 Edition, except where general terms of ordinary dictionary significance are used.

Botanical classification: *Tradescantia andersoniana* 'Good Luck'.

Parentage:

*Female, or seed, parent.*—Unnamed seedling selection of *Tradescantia andersoniana*, not patented.

*Male, or pollen, parent.*—Unnamed seedling selection of *Tradescantia andersoniana*, not patented.

Propagation:

*Type.*—By cuttings.

*Time to initiate roots, summer.*—About three weeks at 20° C.

*Root description.*—Thick, fleshy; dark brown in color.

*Rooting habit.*—Moderate branching; medium in density.

Plant description:

*Plant form and growth habit.*—Herbaceous perennial; compact and upright plant habit; broad inverted triangle; moderately vigorous growth habit.

*Plant height.*—About 45 cm.

*Plant width* (*spread*).—About 53.8 cm.

*Basal branches.*—Length: About 27.6 cm. Diameter: About 5 mm. Internode length: About 5.6 cm. Strength: Moderately strong. Texture: Smooth, glabrous. Color: Close to 137B.

Foliage description:

*Arrangement.*—Alternate; leaves simple and sessile.

*Length.*—About 21.4 cm.

*Width.*—About 1.6 cm.

*Shape.*—Lanceolate.

*Apex.*—Narrowly and long acute.

*Base.*—Sheathing.

*Margin.*—Entire.

*Texture, upper and lower surfaces.*—Smooth, glabrous; at the basal margins, sparsely pubescent.

*Venation pattern.*—Parallel.

*Color.*—Developing leaves, upper surface: Close to 143A. Developing leaves, lower surface: Close to 137B and 143A. Fully expanded leaves, upper surface: Close to 137B; venation, close to N137A. Fully expanded leaves, lower surface: Close to 137C to 137D; venation, close to N137A.

Flower description:

*Flower type and flowering habit.*—Single rotate flowers arranged in simple axillary and terminal clusters; flowers face upright; freely flowering habit with about twelve flowers developing per cluster.

*Fragrance.*—None detected.

*Natural flowering season.*—Plants begin flowering about nine months after planting; long flowering period, plants flower continuously from July through September in The Netherlands.

*Postproduction longevity.*—Flowers last about four days on the plant; flowers not persistent.

*Flower buds.*—Height: About 1 cm. Diameter: About 5 mm. Shape: Ovoid. Color: Close to 137D heavily tinged with close to N177A.

*Flower diameter.*—About 3.8 cm.

*Flower depth.*—About 1.9 cm.

*Petals.*—Quantity per flower: Typically three in a single whorl. Length: About 2 cm. Lobe width: About 1.7 cm. Shape: Broadly ovate. Apex: Broadly acute. Margin: Entire, slightly undulate. Texture, upper and lower surfaces: Smooth, glabrous. Color: When opening and fully opened, upper and surface: Close to N87A and N88B; towards the base, close to N87A. When opening and fully opened, upper and lower surfaces: Close to N87B and N88B; towards the base, close to N87B.

*Sepals.*—Quantity per flower: Typically three in a single whorl. Length: About 1.1 cm. Width: About 3.5 mm. Shape: Ovate. Apex: Acute. Margin: Entire. Texture, upper and lower surfaces: Smooth, glabrous; margins, sparsely pubescent. Color: When opening and fully opened, upper surface: Close to 146B strongly tinged with close to 184A to 184B. When opening and fully opened, upper and lower surfaces: Close to 137D heavily tinged with close to N77A.

*Pedicels.*—Length: About 2.5 cm. Diameter: About 1.5 mm. Angle: Mostly erect. Strength: Moderately strong. Texture: Smooth, glabrous. Color: Close to 182C to 182D.

*Reproductive organs.*—Stamens: Quantity per flower: Typically six. Filament length: About 1 cm. Filament color: Close to 83B; towards the base, close to 83D. Anther shape: Oblong. Anther length: About 2 mm. Anther color: Close to 12A. Pollen amount: Scarce. Pollen color: Close to 12B to 12C. Pistils: Quantity per flower: One. Pistil length: About 1 cm. Stigma shape: Club-shaped. Stigma color: Close to 156B to 156D. Style length: About 9 mm. Style color: Close to 83B. Ovary color: Close to 145D.

*Seed/fruit.*—Seed and fruit development have not been observed on plants of the new *Tradescantia*.

Disease/pest resistance: Plants of the new *Tradescantia* have not been noted to be resistant to pathogens and pests common to *Tradescantia* plants.

Garden performance: Plants of the new *Tradescantia* have been observed to have good garden performance. Plants have been observed to tolerate rain and wind, to be hardy to USDA Hardiness Zone 6 and to tolerate high temperatures of about 35° C.

It is claimed:

1. A new and distinct *Tradescantia* plant named 'Good Luck' as illustrated and described.

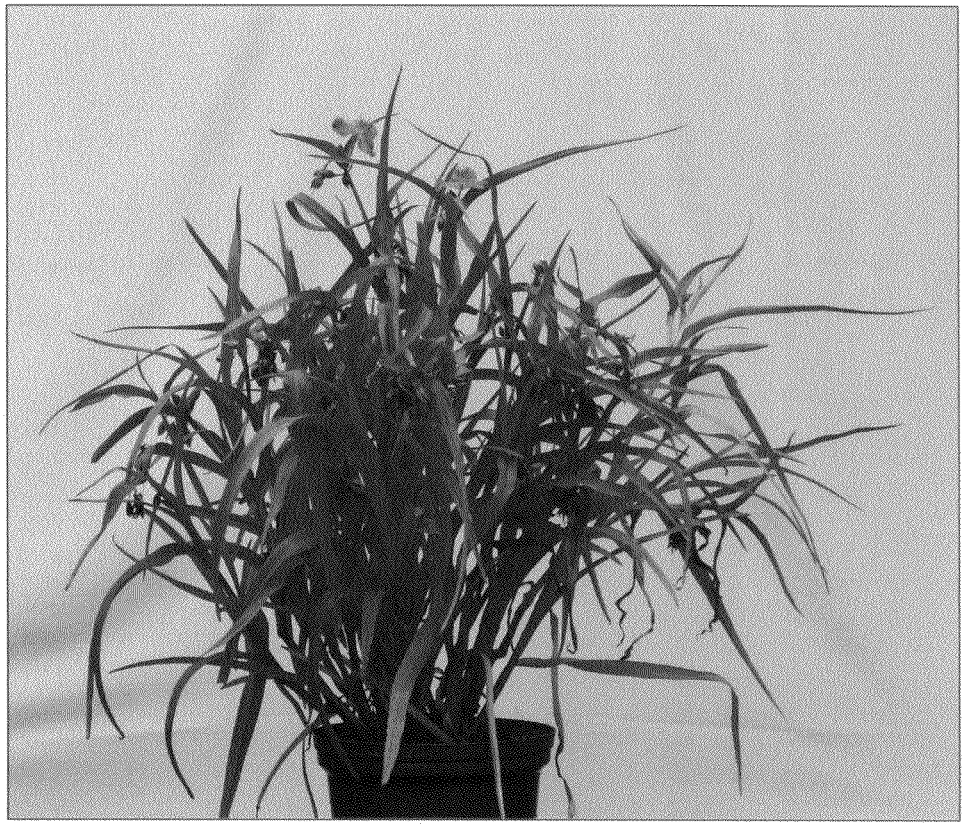

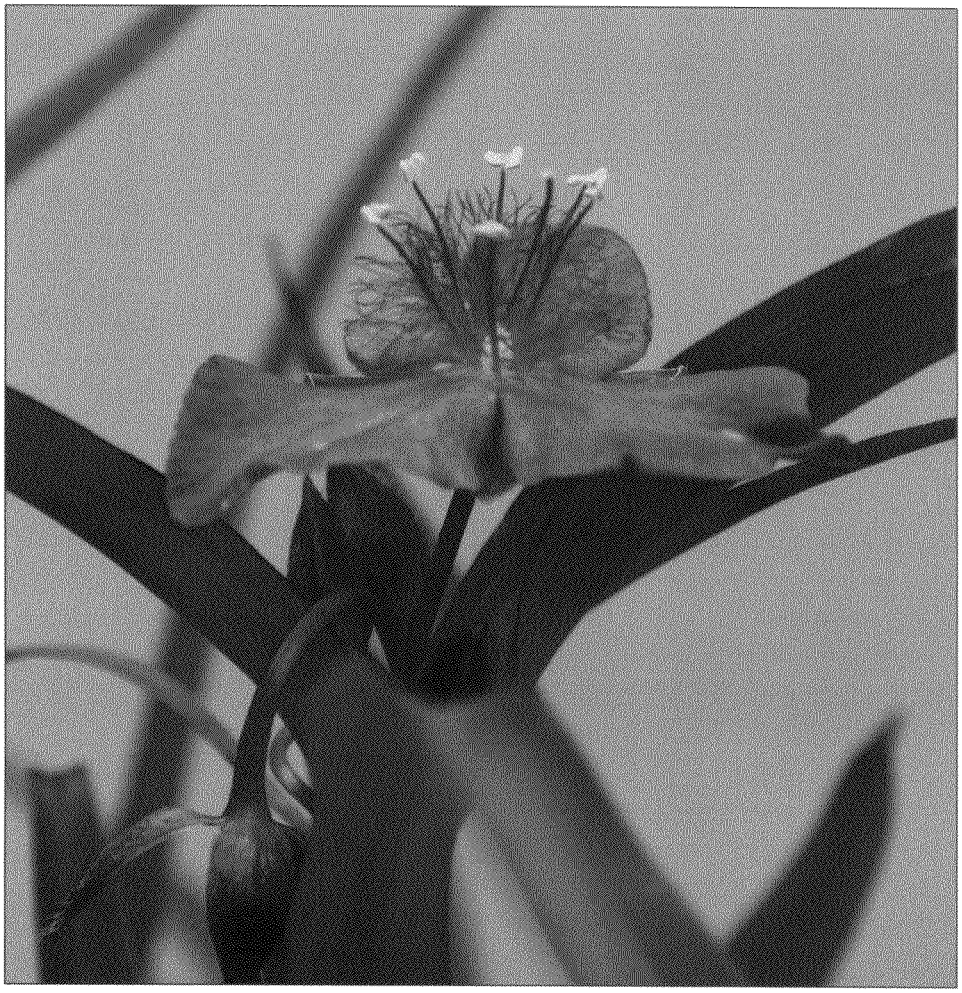
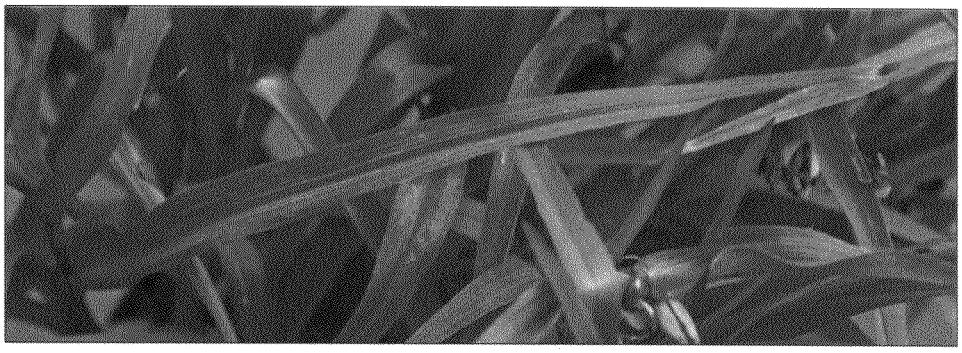

* * * * *